United States Patent [19]

Shiels

[11] Patent Number: 5,061,239

[45] Date of Patent: Oct. 29, 1991

[54] INTUSSUSCEPTION AIR REDUCTION SYSTEM

[76] Inventor: William E. Shiels, 5989 Bagdad Dr., Cincinnati, Ohio 45230

[21] Appl. No.: 473,088

[22] Filed: Jan. 31, 1990

[51] Int. Cl.⁵ .............................................. A61M 37/00
[52] U.S. Cl. ...................................... 604/26; 604/217; 606/197
[58] Field of Search ................... 604/26, 93, 187, 190, 604/217; 606/191, 197

[56] References Cited

U.S. PATENT DOCUMENTS

| | | | |
|---|---|---|---|
| 402,302 | 4/1889 | Casey et al. | 604/26 |
| 576,437 | 2/1897 | Elliott | 604/217 |
| 662,658 | 11/1900 | Steine | 604/26 |
| 4,333,460 | 6/1982 | Miller | 604/217 |
| 4,598,698 | 7/1986 | Siegmund | 604/217 |

*Primary Examiner*—Stephen C. Pellegrino
*Assistant Examiner*—Michael Rafa
*Attorney, Agent, or Firm*—Frost & Jacobs

[57] ABSTRACT

A system for the air reduction of intussusception in infants and children. The system comprises a main tube terminating of its distal end in an enema tip. The proximal end of the main tube is connected to an in-line filter which stops reflux of aerosol and liquid/solid contaminants therebeyond. The filter is connected to a three-way, lever-actuated stopcock which, in turn, is connected to a hand-operated insufflator bulb. The air reduction system is provided with an aneroid gauge. The guage and bulb may constitute a reusable, integral assembly, the remainder of the system being disposable. The entire system may be disposable with a disposable gauge connected ahead of the in-line filter. A reusable gauge may be remotely located and connected to the air reduction system via a branch tube and a T-fitting located between the filter and the three-way valve, all of the system save the remote gauge being disposable. All of the embodiments may be provided with a pop-off valve and adapter located between the filter and the stopcock. All of the embodiments are held and actuated by one hand of the operator, the lever of the stopcock being operated in fingertip, trigger-like fashion.

24 Claims, 4 Drawing Sheets

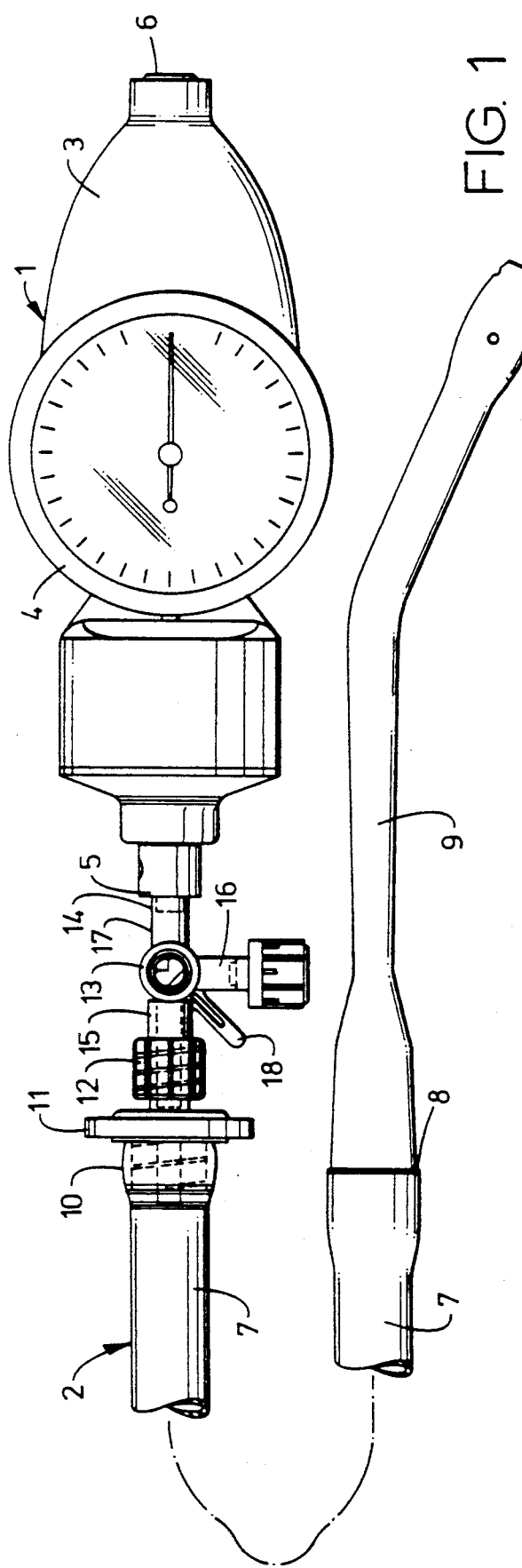
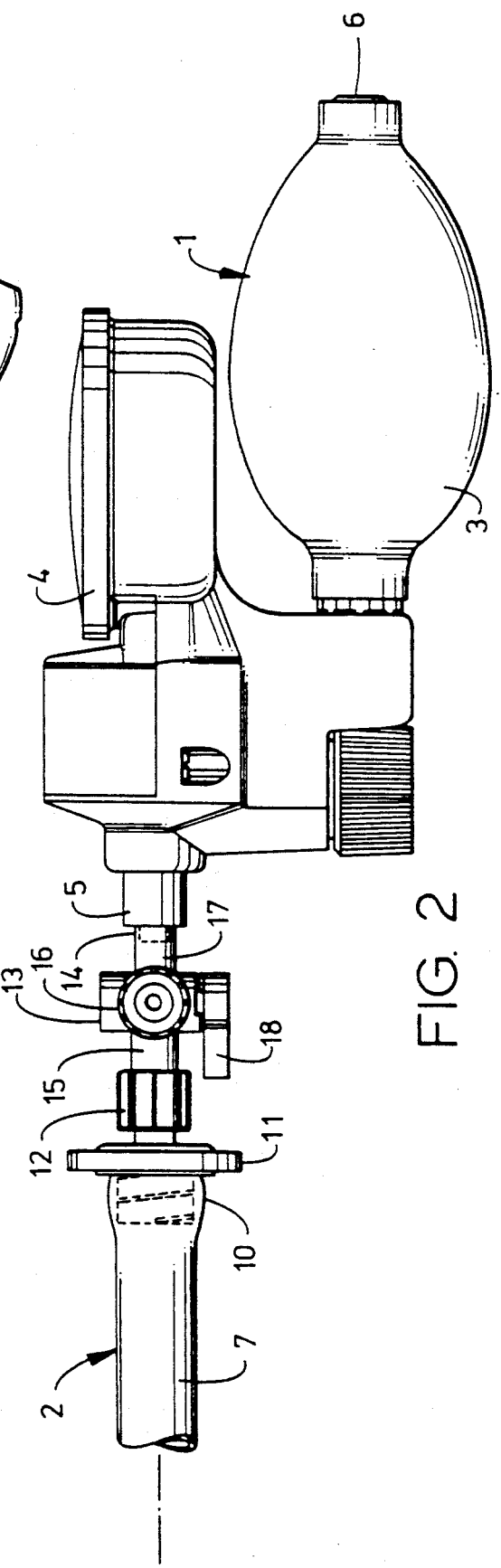
FIG. 1
FIG. 2

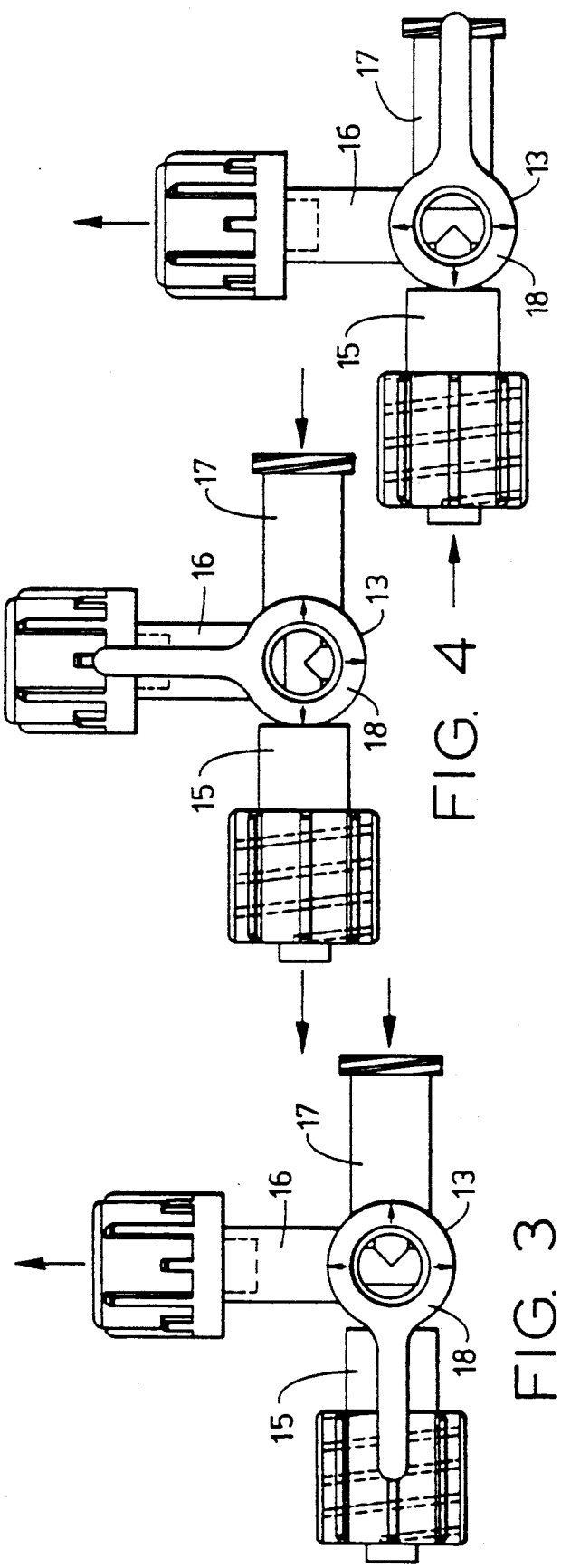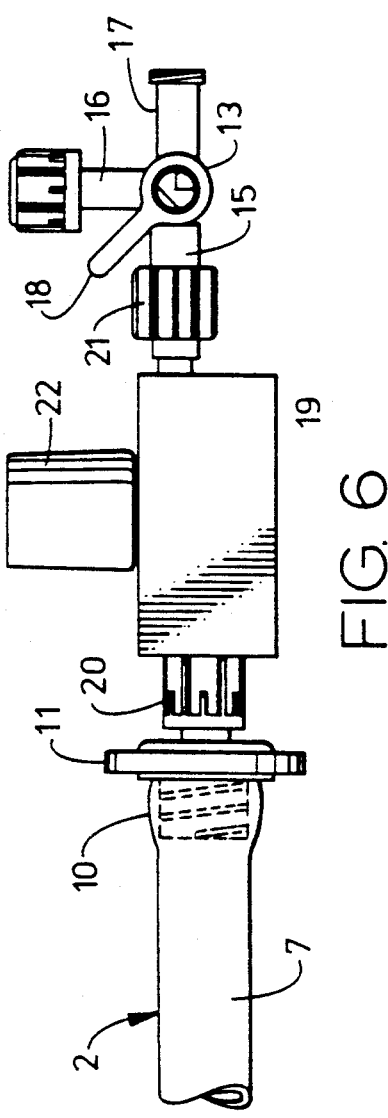

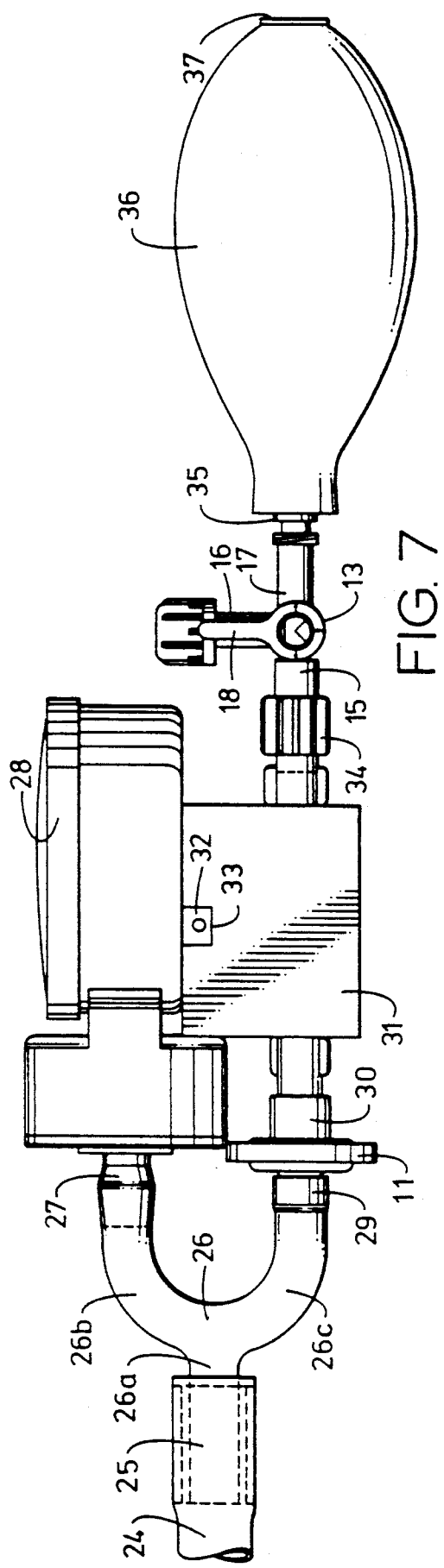
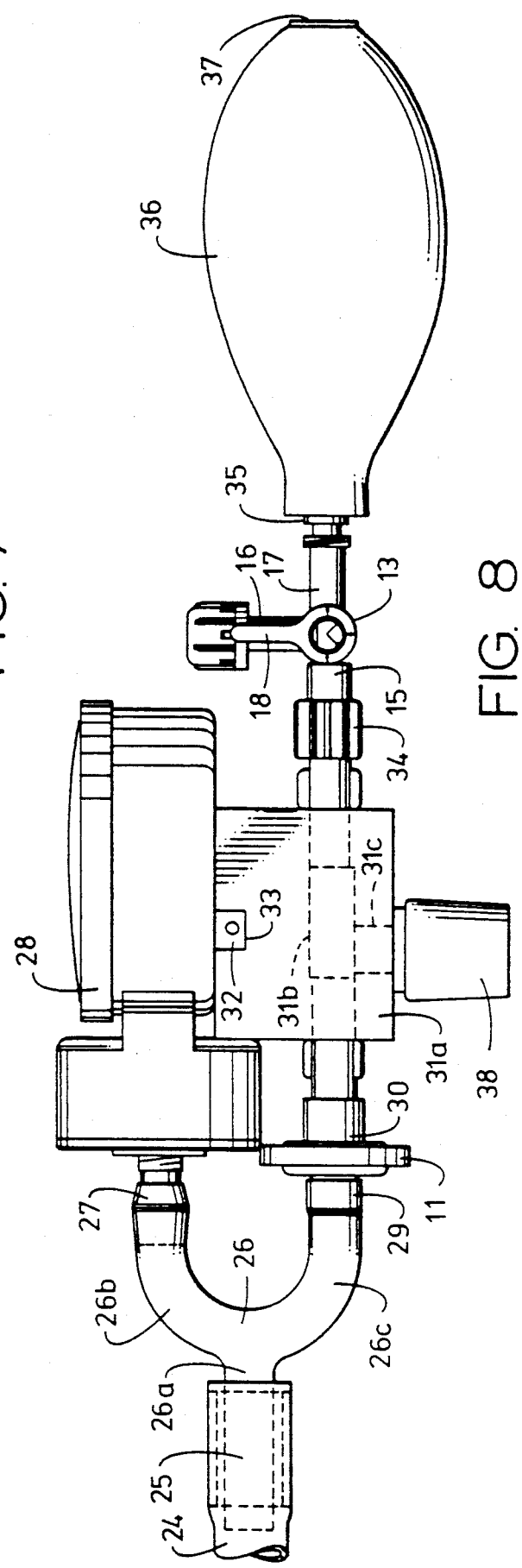
FIG. 7
FIG. 8

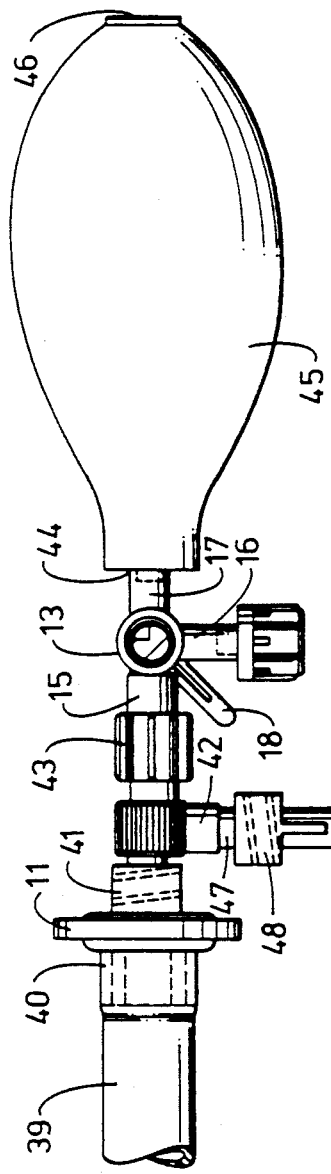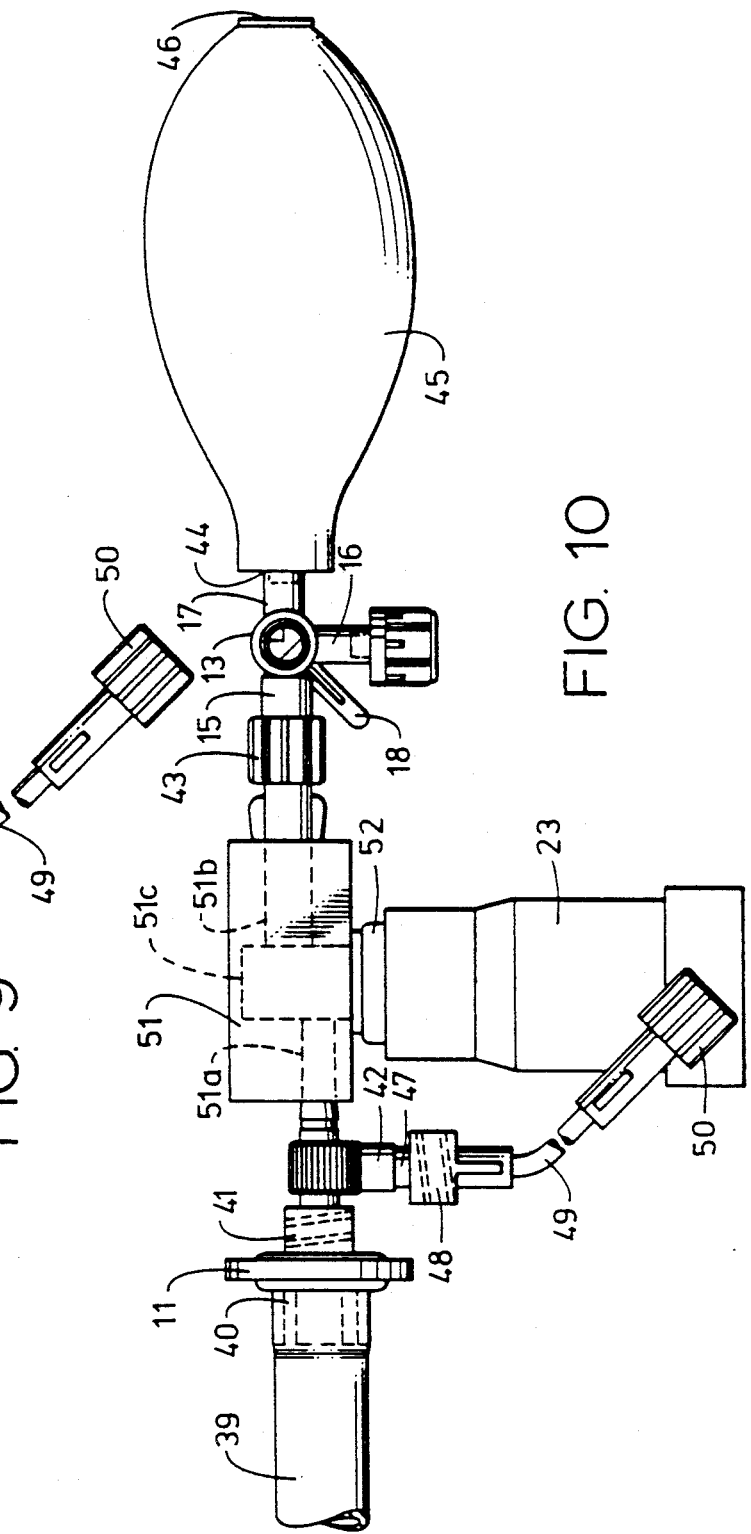
FIG. 9
FIG. 10

INTUSSUSCEPTION AIR REDUCTION SYSTEM

TECHNICAL FIELD

The invention relates to a system for the air reduction of intussusception, and more particularly to such a system wherein all aspects of operation, including insufflation, decompression and aneroid gauge positioning are performed with one hand of the operator.

BACKGROUND ART

Non-surgical initial therapy for intussusception in infants and children has generally constituted hydrostatic reduction under fluoroscopic control using barium or other appropriate water-soluble contrast media. While air reduction of intussusception has long been known and reported, only recently has it gained popularity as an alternative to hydrostatic reduction, having been found to be a more efficient and faster procedure. This, in turn, results in less exposure to radiation both for the patient and the operator. Furthermore, in general, better results have been achieved with air reduction, as compared to hydrostatic reduction.

Prior art workers have devised a number of intussusception air reduction systems. These systems are generally characterized by complexity and awkwardness in operation. They employed various types of gauge devices ranging from mercury manometer systems to sphygmomanometric aneroid gauges. They also employed various types of mechanical and hand-operated air pumping devices. The prior art systems lack the control and simplicity of the present system, and could subject the operator to excessive doses of radiation.

The present invention is based upon the discovery that air reduction of intussusception can be easily and quickly accomplished by a simple and relatively inexpensive system. Unlike the prior art systems, the system of the present invention is hand-held and can be completely operated by one hand of the operator. The system can be held and actuated by either the right or left hand of the operator. The various steps of the procedure are controlled by a lever-actuated three-way stopcock. The lever is controlled in trigger-like fashion by the index finger of the hand holding the system. Unlike hydrostatic systems, the air system of the present invention permits instantaneous decompression by simple manipulation of the above-mentioned index finger. This constitutes an important safety factor. Instantaneous decompression can safely be achieved without contamination, as will be described hereinafter.

Not only can the entire system of the present invention be operated with one hand, but since it is entirely hand-held, it can be operated and held at any level which is preferred by the operator, a level which increases control during the reduction procedure. This is important since the operator can hold the device such that he is able to simultaneously monitor intra-colonic pressure, monitor the reduction procedure on the video monitor, operate the device (insufflate air/decompress as necessary), and control the patient and fluoroscopic tower during the reduction procedure. No other previously described system allows the total control afforded in this design. This control not only simplifies the procedure for more efficiency, but also serves as an important safety element, since improved control over the entire reduction procedure translates into improved safety and fewer unexpected complications.

The single-handed, hand-held operation provides for improved radiation safety, since it allows the radiologist to stand as close to or as far from the radiation source (fluoroscopy table) as desired. This feature is allowed by the tubing length and the one-handed operation design.

As an added safety measure, all embodiments of the present invention may be provided with a pop-off valve, if desired. The air reduction system of the present invention is made up of two basic parts: an insufflator portion and a tube portion, as will be set forth hereinafter. In some embodiments the tube portion is disposable and replaceable. In other embodiments, the entire air reduction system is disposable.

BRIEF DESCRIPTION OF THE INVENTION

According to the invention there is provided a system for the air reduction of intussusception in infants and children. The system comprises an insufflator portion and a tube portion.

In one embodiment, the insufflator portion comprises a hand-actuated bulb and an aneroid pressure gauge constituting a single, integral unit. The tube portion comprises an elongated, preferably transparent tube member terminating at one end in an appropriate enema tip or the like and at the other end in an in-line filter leading to a lever-actuated three-way stopcock. The in-line filter prevents reflux of aerosol and liquid/solid contaminants. In this way, the stopcock, the insufflator portion of the system, the operator and the environment are protected from contamination during operation of the system, as well as during decompression.

The tube portion is disposable and replaceable. The tube portion is connected to the insufflator portion by connecting the three-way stopcock to the insufflator portion by means of a bayonet connection or the like. The insufflator portion is held in one hand of the operator and the lever of the three-way stopcock is manipulated by the index finger of the same hand, in trigger-like fashion. Another embodiment of the present invention is identical to that just described with the exception that an adapter supporting an adjustable pop-off valve is located in the tube portion between the filter and the three-way stopcock.

In a disposable embodiment of the present invention, the main tube is provided with an enema tip or the like at one end and at its other end is connected to one branch of a Y-shaped connecting tube. The second branch of the Y-shaped connecting tube is attached to a disposable aneroid gauge. The third branch of the Y-shaped connector tube is attached to the filter. The filter, in turn, is connected to a bore through a support block which serves as a mounting means for the disposable aneroid gauge. The other end of the bore through the support block is connected to the three-way lever-actuated stopcock. To complete the structure, the stopcock is connected to a hand-actuated bulb. Another embodiment of the present invention is identical to that just described, with the exception that the support block also serves as an adapter, mounting a pop-off valve.

Under some circumstances, it may be desirable to locate the aneroid gauge at a position remote from the bulb, as for example adjacent the viewing screen of the fluoroscope. In such an instance, an embodiment is provided wherein the main tube terminates at one end in an enema tip or the like, and at the other end in the filter. The filter is connected to the three-way stopcock which, in turn, is connected to a hand actuated bulb.

Between the filter and the stopcock a T fitting is provided. A branch tube is connected to the T fitting; the free end of the branch tube is connected to the remote aneroid gauge which may be of either the analog or digital type.

BRIEF DESCRIPTION OF THE DRAWINGS

FIG. 1 is a fragmentary plan view of an air reduction system of the present invention.

FIG. 2 is a fragmentary side elevational view of the air reduction system of FIG. 1.

FIGS. 3-5 are side elevational views of the three-way stopcock, illustrating the positions of its lever and the manner of its operation.

FIG. 6 is an incomplete, fragmentary view of an embodiment similar to that of FIGS. 1 and 2, but provided with an adapter for a pop-off valve.

FIG. 7 is a fragmentary side elevational view of a wholly disposable embodiment of the air reduction system of the present invention.

FIG. 8 is a fragmentary side elevational view of an embodiment similar to that of FIG. 7, but provided with an adapter to receive a pop-off valve.

FIG. 9 is a fragmentary side elevational view of an embodiment of the air reduction system of the present invention with means enabling the remote mounting of the aneroid pressure gauge.

FIG. 10 is a fragmentary side elevational view of an embodiment similar to that of FIG. 9, but provided with an adapter mounting a pop-off valve.

DETAILED DESCRIPTION OF THE INVENTION

A first embodiment of the present invention is illustrated in FIGS. 1 and 2. In this embodiment, the insufflator portion of the air reduction system is generally indicated at 1, and the tube portion is generally indicated at 2. The insufflator portion 1 comprises a commercially available bulb/aneroid pressure gauge unit, the bulb of which is indicated at 3 and the gauge of which is indicated at 4. Such units are available, for example, from Tycos Life Science, Arden, N.C. It will be understood by one skilled in the art that the unit 1 incorporates a one-way valve assembly such that when the bulb is squeezed, air therein exits the outlet 5 of the unit. When the bulb is released, it fills with ambient air through its inlet port 6. The unit 1 is of such size as to be comfortably held in and manipulated by one hand of the operator. The tube portion 2 of the air reduction system comprises a disposable, single-limb tube assembly. The tube assembly, itself, comprises an elongated main tube 7. The main tube 7 may be made of any appropriate material suitable for medical use, such as polyvinylchloride. The tube 7 is preferably transparent, allowing the operator to visually detect refluxed material during the procedure.

One end of the main tube 7 is connected as at 8 to an appropriately sized and shaped, conventional enema tip 9.

The other end of main tube 7 is connected as at 10 to an in-line filter 11. The in-line filter 11 is a commercially available filter containing a hydrophobic acrylic polymer with a 0.2 micron pore size. The filter stops reflux of aerosol and liquid/solid contaminants. Filters of this type are sold, for example, by Gelman Sciences, Inc. of Ann Arbor, Mich. under the mark "Versapor-H."

The filter 11 is connected as at 12 to one port of a three port (or three-way) lever-actuated stopcock 13.

The stopcock 13 completes the tube portion 2 of the air reduction system. It is preferable that all of the junctures 8, 10 and 12 are bonded with adhesive means, assuring an air and fluid tight joint at each position. Both the insufflator portion 1 and the tube portion 2 of the air reduction system may be provided in the form of pre-packaged units. In use, the three-way stopcock 13 is removably connected to the insufflator portion as at 14, by a bayonet mount or the like.

The three-way stopcock 13 is illustrated in FIGS. 3, 4 and 5. The stopcock 13 has a port 15 connected to the filter 11, and exhaust port 16 and a port 17 for connection to the insufflator portion of the air reduction system. The three-way stopcock 13 is actuated by a lever 18. When the lever 18 is in the position illustrated in FIG. 3, the port 15 is closed and the ports 16 and 17 are open. When the lever is in the position illustrated in FIG. 4, the port 16 is closed and the ports 15 and 17 are open. Similarly, when the lever 18 is in the position illustrated in FIG. 5, the ports 15 and 16 are open and the port 17 is closed. In other words, whatever port the lever 18 lies along is closed, with the other two ports being open.

The embodiment of FIGS. 1 and 2 having been described in detail, its manner of use may now be set forth. When air reduction of intussusception is indicated, the enema tip 9 is placed in the rectum of the patient and the buttocks are taped together securely. The proximal end of the tube portion 2 is sealed by locating the three-way stopcock lever 18 in the position shown in FIG. 3, closing port 15. Thereafter, the insufflator portion 1 is connected to the port 17 of the three-way stopcock. When properly mounted, the stopcock is positioned with the lever on the underside of the insufflator portion 1 (as shown in FIGS. 1 and 2), enabling the lever to be easily operated by the index finger of the operator's right or left hand, i.e., the same hand with which the operator grasps the insufflator portion 1. In the attachment of the insufflator portion 1 to the port 17 of the three-way valve 13, care should be taken to orient the aneroid gauge 4 for easy reading.

After connecting the insufflator portion 1 with the tube portion 2, the lever 18 of the three-way stopcock 13 is located in the position illustrated in FIG. 4, insuring one-way flow of air into the patient.

At this point, air is insufflated into the colon under direct fluoroscopic control, with one-handed operation allowing complete control of colonic distention and movement of the intussusceptum. It will be apparent to one skilled in the art that the stopcock allows immediate decompression of the system at any time during the procedure. In other words, when the lever is shifted to the position shown in FIG. 5, venting is accomplished via port 16. If multiple reduction attempts are required, this stopcock decompression trigger-like control facilitates relaxation of the colon without requiring removal of the enema tip.

From the above, it will be noted that all aspects of operation, including insufflation, decompression and aneroid gauge positioning, are performed with one hand. The operator can operate the bulb 3, and stopcock 13, watch the gauge 4 and the fluoroscope monitor at the same time, without having to be in the x-ray field. Nothing is required to be wall or table mounted. The one-handed, trigger-like fingertip actuation of the three-way stopcock lever 18 allows for complete control of the air reduction system at all times, with instantaneous decompression being easily achievable at any point during the procedure. Furthermore, instantaneous decompression can be safely achieved without contamination of the insufflator portion 1, the operator, or the environment, by virtue of filter 11.

At the end of the procedure, the tube portion 2, including three way stopcock 13, is detached from the insufflator portion 1 and disposed of. For the next procedure, a new tube portion is attached to the insufflator portion 1.

FIG. 6 illustrates a modification of the embodiment of FIGS. 1 and 2. Like parts have been given like index numerals. The embodiment of FIG. 6 differs from that of FIGS. 1 and 2 only in that the pop-off or relief valve adaptor 19 is connected as at 20 and 21 between the filter 11 and the three-way stopcock 13. The adapter 19 has a passage therethrough (not shown) connecting the stopcock port 15 with the filter 11. The adapter 19 has a branch passage, from the last mentioned passage, leading to the hollow, slightly tapered fitting 22. The fitting 22 is adapted to be received in the end of a commercially available relief or pop-off valve of the type shown at 23 in FIG. 10. The pop-off or pressure relief valve 23 is settable to any appropriate pop-off pressure and should be set and tested prior to each procedure. An exemplary pop-off pressure is about 120 mm Hg. The pop-off or pressure relief valve 23 serves as an additional safety device for the air reduction system. Again, the connections 20 and 21 are preferably bonded.

In instances where the adapter 19 is not provided by the manufacturer, but it is desired that it be added to the embodiment of FIGS. 1 and 2, the adapter 19 is preferably connected and bonded to the port 17 of the existing three-way stopcock 13 and the lever 18 of the three-way stopcock 13 should be permanently located in the position illustrated in FIG. 4. A second three-way stopcock (not shown), identical to three-way stopcock 13 should be connected between the adapter and the outlet 5 of the insufflator portion 1. It is this second stopcock which will be used by the operator to control the procedure. The original stopcock serves simply as a connection between the adapter and the filter 11. This is true because the joint 12 is bonded and cannot be opened for insertion of the adapter 19 between filter 11 and the original three-way stopcock 13.

A fully disposable air reduction system is illustrated in FIG. 7. In this embodiment the distal end (not shown) of the main tube 24 will be provided with an enema tip (not shown) equivalent to the enema tip 9 of FIG. 1. The proximal end of the main tube 24 is connected as at 25 to one branch 26a of a Y-shaped connector tube 26. Another branch 26b of the Y-shaped connector tube 26 is attached at 27 to a disposable aneroid pressure gauge 28. The third branch 26c of the Y-shaped connector tube is attached as at 29 to an in-line filter, identical to the filter of the embodiment of FIGS. 1 and 2, and indicated by the same index numeral 11.

The in-line filter 11 is connected, as at 30, to a support block 31. The purpose of support block 31 is to mount the disposable aneroid gauge 28. The attachment of aneroid gauge 28 to support block 31 may be accomplished in any appropriate manner. For example, the aneroid gauge 28 may be provided with one or more lugs 32 on its rearward side. The at least one lug 32 may be received in a slot 33 formed in support block 31. The lug 32 may be mechanically (as by pinning or the like) or adhesively bonded in slot 33.

The support block 31 is attached, as at 34 to a three-way, lever-actuated stopcock, identical to that of FIGS. 1–6, and given the same index numeral 13. To this end, the stopcock 13 has ports 15, 16 and 17, together with lever 18. It will be understood that the stopcock 18 functions in the same manner described with respect to FIGS. 3–5. Support block 31 has a passage therein (not shown) connecteing filter 11 and stopcock port 15.

The port 17 of three-way stopcock 13 is attached to the outlet 35 of a hand-actuated bulb 36. The bulb 36 is of the known one-way type wherein, when the bulb is squeezed, air therein exits bulb outlet 35. When the bulb is released, ambient air enters therein through bulb inlet 37.

Since the entire structure of the air reduction system of FIG. 7 is intended to be disposable, the joint (not shown) between the distal end of main tube 24 and the enema tip, as well as the joints 25, 27, 29, 30 and 34 are preferably adhesively bonded. The same is true of the joint between three-way stopcock port 17 and bulb 36, if desired. It will be understood by one skilled in the art that the manner of use of the embodiment of FIG. 7 is identical to that described with respect to the embodiment of FIGS. 1 and 2. In the embodiment of FIG. 7, for purposes of clarity, the three-way stopcock 13 has been shown in an upright position. Preferably, when the parts are assembled, the lever 18 of the three-way stopcock 13 will be oriented in the manner illustrated in FIGS. 1 and 2, so as to be easily accessible to the index finger of the right or left hand of the operator. The same is true of the embodiment of FIG. 8, next to be described.

The embodiment of FIG. 8 is substantially identical to that of FIG. 7 and like parts have been given like index numerals. The only difference between the embodiment of FIGS. 7 and 8 lies in the fact that the support block 31a of FIG. 8 not only has the passage 31b (not shown in FIG. 7) therethrough between the in-line filter 11 and the three-way stopcock 13, but also has a branch passage 31c leading to a fitting 38, identical to fitting 22 of FIG. 6, and intended to support a pop-off or relief valve of the type shown at 23 in FIG. 10. Except for this additional safety feature, the embodiment of FIG. 8 is otherwise identical in structure and mode of use to the embodiment of FIG. 7.

Under some circumstances, the operator may prefer to have the aneroid gauge of the air reduction system remotely located. For example, the operator may wish the aneroid gauge to be located adjacent the monitor of the fluoroscope. The aneroid gauge may be of the analog type, or in the form of a digital transducer, so long as the digital readout thereof is sufficiently instantaneous.

FIG. 9 illustrates a wholly disposable embodiment of an air reduction system equipped for remote location of the aneroid gauge. This embodiment comprises a main tube 39 which may be identical to the main tube 7 of the embodiment of FIGS. 1 and 2 and terminating at its distal end in a conventional enema tip (not shown).

The proximal end of main tube 39 is connected as at 40 to an in-line filter identical to the filter of FIGS. 1 and 2 and given the same index numeral 11. The in-line filter 11 is connected as at 41 to a T-fitting 42, the purpose of which will be apparent hereinafter. The T-fitting 42 is connected as at 43 to a three-way stopcock identical to that of FIGS. 1 and 2 and given the same index numeral 13. The three-way stopcock 13 is provided with ports 15, 16 and 17, together with actuating lever 18, and operates in the same manner described with respect to FIGS. 3–5. The port 17 of the three-way stopcock 13 is connected as at 44 to a one-way bulb 45. The bulb 45 is of the one-way type such a the bulb 36 described with respect to FIG. 7, having its outlet at the juncture 44 and being provided with an inlet 46. Since the embodiment of FIG. 9 is intended to be wholly disposable, the juncture (not shown) of the distal end of main tube 39 and the enema tip, together with junctures 40, 41, and 43 are preferably bonded together. The same is true of juncture 44, if desired.

The T-fitting 42 has a branch outlet 47 connected, as at 48, to a branch tube 49. The branch tube 49 may be of any length required and its distal end terminates in a connector 50 adapted to be removably attached to the inlet of the remote aneroid gauge.

It will be apparent to one skilled in the art that the mode of operation of the embodiment of FIG. 9 is otherwise identical to that described with respect to the embodiment of FIGS. 1 and 2. Since the in-line filter 11 is located ahead of T-fitting 42, the remote aneroid gauge is fully protected from contamination and is, of course, reusable.

FIG. 10 illustrates an embodiment of the air reduction system substantially identical to the embodiment of FIG. 9, and like parts have been given like index numerals. The embodiment of FIG. 10 differs from that of FIG. 9 only in that a pop-off or relief valve adapter 51 is located between T-fitting 42 and three-way stopcock 13. Again, preferably the joints between these elements are bonded.

The adapter 51 contains passages 51a, 51b and 51c directly connecting T-fitting 42 to three-way stopcock 13. The passageway 51c additionally connects to hollow fitting 52, identical to fitting 22 of FIG. 6. The Fitting 52 supports pop-off or relief valve 23.

It will be understood by one skilled in the art that the T-fitting 42 in the embodiments of FIGS. 9 and 10 and the adapter 51 in the embodiment of FIG. 10 may, during assembly, be given any appropriate orientation so as to comfortably not interfere with the operation of the air reduction system. Again, in these embodiments, the lever 18 of the three-way stopcock 13 is oriented in the manner described with respect to the embodiment of FIGS. 1 and 2.

From the above description, it will be apparent that all embodiments of the present invention are capable of being held and actuated by one hand of the operator. The fingertip, trigger-like actuation of the three-way stopcock lever 18, allows for complete control of the system with the capability of instantaneous decompression at any time during the procedure.

Modifications may be made in the invention without departing from the spirit of it.

What is claimed is:

1. Apparatus for the air reduction of intussusception comprising an elongated main tube terminating at its distal end in an enema tip, the proximal end of said main tube being connected to an in-line filter capable of stopping reflux of aerosol and liquid/solid contaminants, a three-way lever-actuated stopcock, said stopcock having first, second and third ports, said first and third ports being coaxial, said second port being perpendicular to said first and third ports and opening to atmosphere, said first port being connected to said filter, a hand actuated one-way bulb having an outlet means for the expulsion of air therein when said bulb is squeezed and a separate inlet for the intake of air when said bulb is released, said third port of said stopcock being connected to said bulb outlet means, said stopcock being shiftable between a first position wherein said first port is closed sealing the remainder of said apparatus from atmosphere and said outlet means of said bulb, the outlet means of said bulb being connected to atmosphere via said second port, a second position closing said second port leading to atmosphere and connecting said bulb outlet means with the remainder of said apparatus for insufflation, and a third position closing said third port to said bulb outlet means and connecting the remainder of said apparatus to atmosphere via said second port for decompression, said stopcock lever being so positioned as to be shiftable by the index finger of the operator's hand which holds and actuates said bulb, and an aneroid pressure gauge connected to said apparatus between said main tube and said bulb.

2. The apparatus claimed in claim 1 wherein said bulb and said aneroid pressure gauge comprise an integral assembly.

3. The apparatus claimed in claim 1 including a Y-shaped connector tube having first, second and third branches, said first branch being connected to said distal end of said main tube, said second branch being connected to said aneroid pressure gauge, said third branch being connected to said filter, a support block having a passage therethrough connected between said filter and said first stopcock port, said aneroid pressure gauge being mounted on said support block.

4. The apparatus claimed in claim 1 including a T-fitting connected between said filter and said first stopcock port, a branch tube having first and second ends, said first end of said branch tube being connected to said T-fitting, said second end of said branch tube being connected to said aneroid pressure gauge, said branch tube being of such length as to enable remote mounting of said aneroid pressure gauge.

5. The apparatus claimed in claim 1 wherein said main tube is transparent.

6. The apparatus claimed in claim 1 wherein said main tube is made of polyvinylchloride.

7. The apparatus claimed in claim 1 wherein said in-line filter contains a hydrophobic acrylic polymer with a pore size of about 0.2 micron.

8. The apparatus claimed in claim 1 including an adapter block having a passage therethrough connected between said filter and said first port of said stopcock, a hollow fitting mounted on said adapter block; said adapter block having a branch passage leading to said fitting, an adjustable pressure relief valve being mounted on said fitting.

9. The apparatus claimed in claim 1 wherein said connections between the distal end of said main tube and said enema tip, the proximal end of said main tube and said filter, and said filter and said first port of said stop cock are adhesively bonded.

10. The apparatus claimed in claim 2 wherein said main tube is transparent.

11. The apparatus claimed in claim 2 wherein said main tube is made of polyvinylchloride.

12. The apparatus claimed in claim 2 wherein said in-line filter contains a hydrophobic acrylic polymer with a pore size of about 0.2 micron.

13. The apparatus claimed in claim 2 including an adapter block having a passage therethrough connected between said filter and said first port of said stopcock, a hollow fitting mounted on said adapter block; said adapter block having a branch passage leading to said fitting, an adjustable pressure relief valve being mounted on said fitting.

14. The apparatus claimed in claim 2 wherein all of said connections save that between said stopcock third port and said bulb/gauge assembly are adhesively bonded.

15. The apparatus claimed in claim 3 wherein said main tube is transparent.

16. The apparatus claimed in claim 3 wherein said main tube is made of polyvinylchloride.

17. The apparatus claimed in claim 3 wherein said in-line filter contains a hydrophobic acrylic polymer with a pore size of about 0.2 micron.

18. The apparatus claimed in claim 3 including a hollow fitting mounted on said support block, said support block having a branch passage leading to said hollow fitting, an adjustable pressure relief valve being mounted on said hollow fitting.

19. The apparatus claimed in claim 3 wherein all of said connections are adhesively bonded.

20. The apparatus claimed in claim 4 wherein said main tube is transparent.

21. The apparatus claimed in claim 4 wherein said main tube is made of polyvinylchloride.

22. The apparatus claimed in claim 4 wherein said in-line filter contains a hydrophobic acrylic polymer with a pore size of about 0.2 micron.

23. The apparatus claimed in claim 4 including an adapter block having a passage therethrough connected between said filter and said first port of said stopcock, a hollow fitting mounted on said adapter block; said adapter block having a branch passage leading to said fitting, an adjustable pressure relief valve being mounted on said fitting.

24. The apparatus claimed in claim 4 wherein said connections between said distal end of said main tube and said enema tip, said proximal end of said main tube and said filter, said T-fitting and said filter, said T-fitting and said branch tube, said T-fitting and said stop cock, and said stop cock and said bulb are adhesively bonded.

* * * * *